United States Patent

Malentacca

[11] Patent Number: 5,735,690
[45] Date of Patent: Apr. 7, 1998

[54] SET OF DRILLS FOR THE BORING OF THE CORONARY PART OF DENTAL RADICULAR CANALS

[75] Inventor: Augusto Malentacca, Rome, Italy

[73] Assignee: Maillefer Instruments S.A., Switzerland

[21] Appl. No.: 666,749

[22] Filed: Jun. 19, 1996

[30] Foreign Application Priority Data

Jan. 17, 1996 [CH] Switzerland ................. 125/96

[51] Int. Cl.$^6$ ................................. A61C 5/02
[52] U.S. Cl. ................................. 433/102
[58] Field of Search ...................... 433/102, 224

[56] References Cited

U.S. PATENT DOCUMENTS

| | | | |
|---|---|---|---|
| 4,661,061 | 4/1987 | Martin | 433/102 |
| 4,850,867 | 7/1989 | Senia et al. | 433/102 |
| 5,026,284 | 6/1991 | Martin | 433/102 |
| 5,035,617 | 7/1991 | McSpadden | 433/102 |
| 5,257,934 | 11/1993 | Cossellu | 433/102 |

*Primary Examiner*—Cary E. O'Connor
*Attorney, Agent, or Firm*—Silverman, Cass & Singer, Ltd.

[57] ABSTRACT

The length of the active part of each drill of the set is inversely proportional to the diameter of the cutting edge of each drill, that prevents the drills of the set being too much engaged in the coronary canal, since the depth of the working depends with precision from the used drill.

4 Claims, 2 Drawing Sheets

N°1

N°2

N°3

N°4

N°5

N°6

SET OF DRILLS FOR THE BORING OF THE CORONARY PART OF DENTAL RADICULAR CANALS

BACKGROUND OF THE INVENTION

1. Field of the Invention

The present invention relates to a set of drills for the boring of the coronary part of the dental radicular canals, of the type called of Gates, comprising a stem ending, at its front extremity, by a cutting edge provided with at least one helicoidal groove presenting a cutting edge and ending, at its rear extremity, by a handle, set in which the diameter of the said cutting edge varies from a drill to the other one.

2. Description of the Prior Art

Such sets of drills are known.

The dentist who bores the coronary third of the length of dental radicular canals, after having effected manually the first step, called of catheterism, which consists in engaging into the radicular canal a very fine instrument up to the apical foramen, uses thereafter drills of Gates, mechanically driven by means of a hand-piece, either while going from the drill the cutting head of which is of the smallest diameter up to the drill the head of which is of the largest diameter, in an operation called "step-back", or while starting with the drill the diameter of the cutting head of which is the largest for ending with the drill the cutting head of which is of the smallest diameter, in an operation called "crown-down". The dentist must watch to adjust the depth of the boring in function of the used drill, the drill the head of which is of the smallest diameter being engaged the most deeply and the drill the head of which is of the largest diameter being engaged the less deeply. The boring of the coronary part of the radicular canal has thus a bell mouthed shape which favorises the obturation.

Obviously, the dentist can use, for the determination of the depth at which each drill must penetrate, guide washers engaged on the stem of the said drills. However, this needs from the dentist some ability and risks of mistakes are not excluded.

SUMMARY OF THE INVENTION

The object of the present invention is to remove this drawback.

This object is achieved by the fact that the length of the active part of each drill of the set, that is to say the length of the said stem and of the cutting head varies in an inverse ratio with the diameter of the said head.

The various features of the invention will be apparent from the following description, drawings and claims, the scope of the invention not being limited to the drawings themselves as the drawings are only for the purpose of illustrating ways in which the principles of the invention can be applied. Other embodiments of the invention utilising the same or equivalent principles may be used and structural changes may be made as desired by those skilled in the art without departing from the present invention and the purview of the appended claims.

DESCRIPTION OF THE PREFERRED EMBODIMENTS

Figure 1:
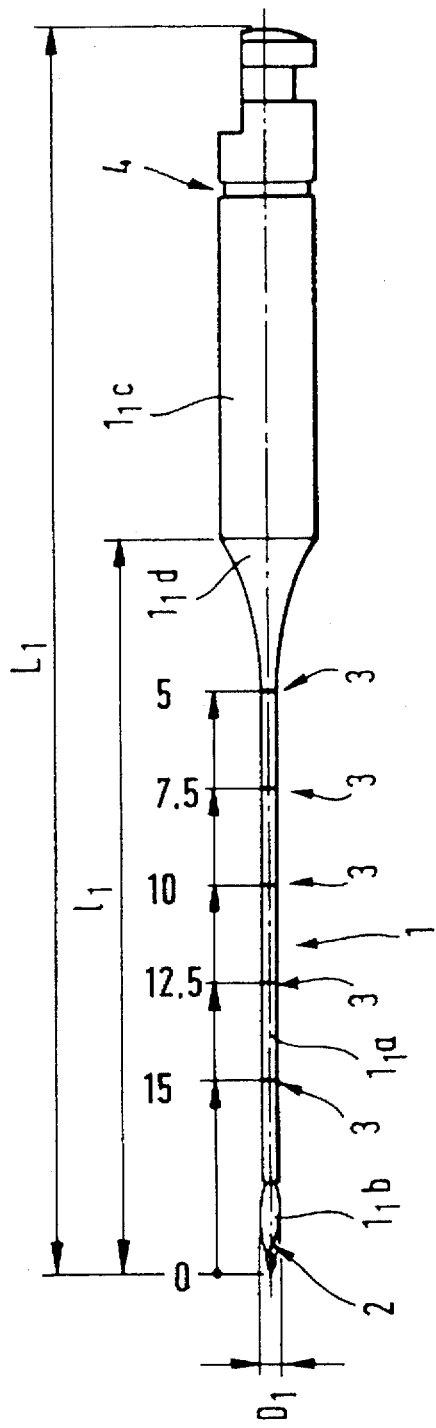
FIG. 1 is an elevational view of a drill of Gates.
Figure 2A:
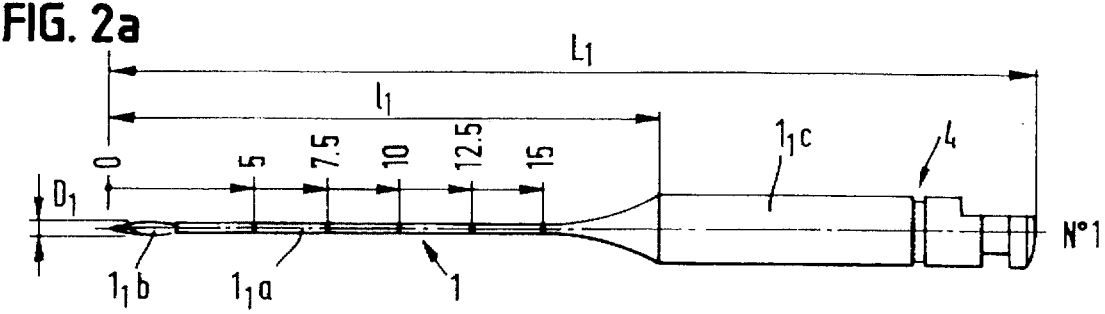
FIGS. 2a through 2f are respectively additional views of six Gates-type drills constituting a set of drills numbered drill No. 1 through drill No. 6, respectively.
Figure 2B:
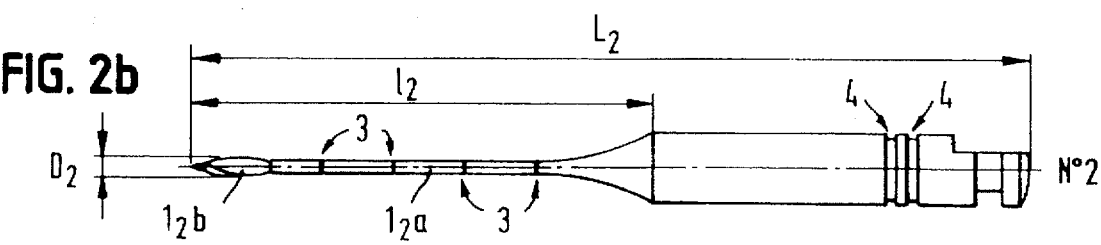
Figure 2C:
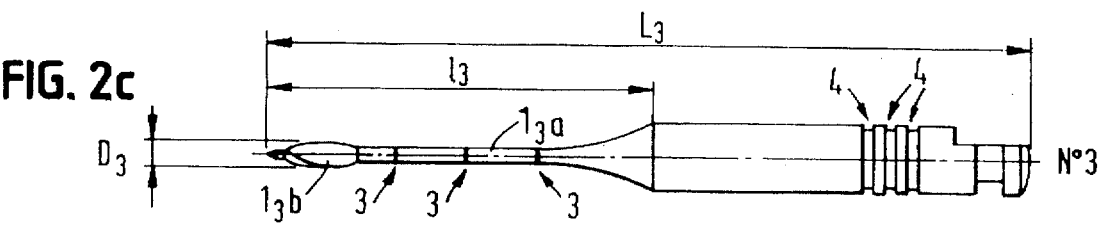
Figure 2D:
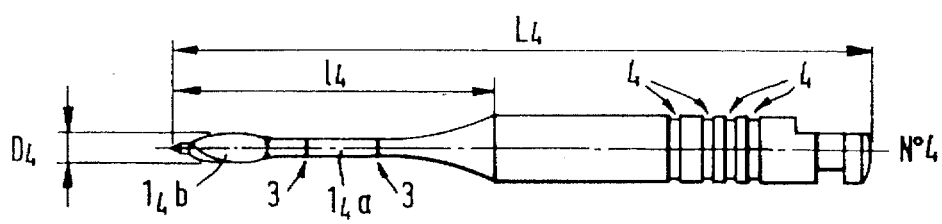
Figure 2E:
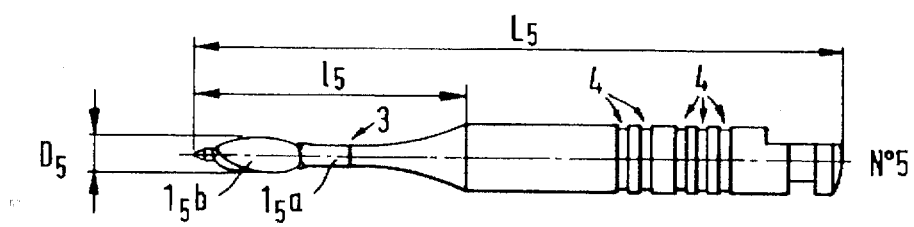
Figure 2F:
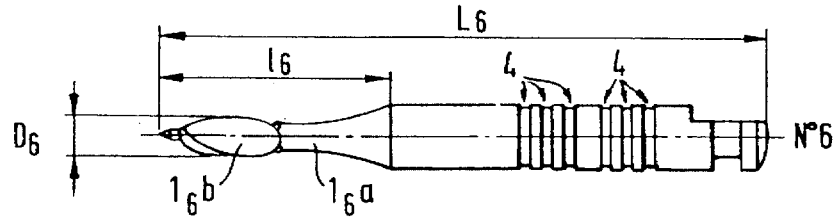

The drill illustrated in FIG. 1, designated by reference $1_1$, which is the first one of the set represented in FIG. 2, comprises a cylindrical stem $1_1a$ and, at its front extremity, a cutting head $1_1b$ and, at its rear extremity, a handle $1_1c$ intended to be engaged into a hand-piece serving to the mechanical drive of the drill. The stem 1 will be realised in any alloy showing a high flexibility.

The cutting head $1_1b$ has the shape of a revolution body the generatrix of which is constituted by an arc of circle and which shows three helicoidal grooves 2, having a cutting edge. The number of the grooves 2 can be different from three.

In the case of the drill of FIG. 1, which constitutes the drill No 1 of the set, the diameter $D_1$ of the cutting head $1_1b$ is of 0.50 mm. The total lenght $L_1$ of the drill is of 32 mm. The length of its active working part $l_1$, that is to say of its stem $1_1a$ and of the cutting head $1_1b$, up to the end of its bell-mouthed part $1_1d$ providing the connection between the stem $1_1a$ and the handle $1_1c$ is of 19 mm.

The stem $1_1a$ is provided, at distances of 5.0, 7.5 10.0, 12.5 and 15.0 mm from the extremity of the drill, respectively, lines or rings 3 for indicating the depth at which the drill is engaged in the dental canal. The guide lines or rings can be realised by engraving, by means of a laser or also merely by means of a colored print.

In the second drill of the set, bearing the No 2, the diameter $D_2$ of the cutting head, designated by $1_2b$, is of 0.7 mm, the total length $L_2$ of the drill being of 28.5 mm and the length of its active part $l_2$ of 15.9 mm. The stem, designated by $1_2a$, of this drill is provided with only four annular guide lines 3.

So far as the third drill of the set is concerned, carrying the No 3, the diameter $D_3$ of its head $1_3b$ is of 0.9 mm, its total length $L_3$ of 26.4 mm and the length of its active part $l_3$ of 13 mm. The stem, designated by $1_3a$, of this drill is provided with three annular guide lines 3.

The drill No 4 of the set is provided with a cutting head $1_4b$, the diameter $D_4$ of which is of 1.10 mm. Its total length $L_4$ is of 24.3 mm and the length of its active part $l_4$ of 11.3 mm. Its stem, designated by $1_4a$, is provided with two annular guide lines 3.

The head, designated by $1_5b$, of the drill No 5, has a diameter $D_5$ of 1.30 mm. The total length $L_5$ of this drill is of 22.5 mm and the length of its active part $l_5$ of 9.5 mm. The stem, designated by $1_5a$, of this drill is provided with only one annular guide line 3.

Finally, the sixth and last drill of the set, carrying the No 6, is provided with a head $1_6b$ the diameter $D_6$ of which is of 1.50 mm. Its total length $L_6$ is of 21 mm and the length of its active part $l_6$ of 8 mm. The stem, which is very short, designated by $1_6a$, of this drill is not provided with any annular guide line.

It is to be noted that the handle of each of the drills of the set is provided with one or more annular grooves 4 the number of which corresponds to the No of the drill and which are intended to permit to the dentist to identify easily the several drills of the set. These grooves 4 can be replaced by colored rings.

The reduction of the length of the active part of the several drills of the set follows a geometrical progression the ratio of which is 0,84 mm, while the variation of the diameters of their cutting head follows an arithmetic progression.

The ratio of the geometrical progression of the reduction of the length of the stems of the drills of the set could be different from 0.84. This reduction could also be based on an arithmetic progression, of 2.2 mm, for example, for each No of the drills of the set.

The following table shows the values of the diameters of the cutting edge, the length of the active or working part, the total length and the number of the guide lines or rings of each of the six drills of Gates of the set represented in FIG. 2.

|          | diameter | working length | total length | number of rings |
|----------|----------|----------------|--------------|-----------------|
| Gate No 1 | 0.50 | 19 mm   | 32 mm   | 5 |
| Gate No 2 | 0.70 | 15.9 mm | 28.9 mm | 4 |
| Gate No 3 | 0.90 | 13.4 mm | 26.4 mm | 3 |
| Gate No 4 | 1.10 | 11.3 mm | 24.3 mm | 2 |
| Gate No 5 | 1.30 | 9.5 mm  | 22.5 mm | 1 |
| Gate No 6 | 1.50 | 8.0 mm  | 21.0 mm | 0 |

Owing to the present set of drills, the dentist, who acts according to the method called "step-back" or according to the method called "crown-down", realizes a bell-mouthed boring of the coronary part of the radicular canal, the conicity of the bored canal corresponding to a desired predetermined value. He saves time and works with more safety, without any risk, with each drill of the set, the length of which is function of the diameter of its cutting edge, of penetrating too deeply into the canal in course of boring.

Moreover, the drills of the highest No. being short, the access into the mouth is more easy.

I claim:

1. A set of Gates-type drills for boring the coronary part of dental radicular canals comprising, each drill including an active part having a stem and a cutting head with at least one helicoidal groove presenting a cutting edge, each active part having a first rear extremity terminating at a handle and a second front extremity terminating at said cutting head, the overall length of said drills being different for each drill of the set, the length of each drill between the first and second extremities varying in inverse ratio with respect to the diameter of the respective cutting head.

2. A set of drills as claimed in claim 1 in which the length of each drill between the first and second extremities varies respectively between each drill of the set according to a geometrical progression, while the diameter of each cutting head of each drill varies respectively between each drill of the set according to an arithmetic progression.

3. A set of drills as claimed in claim 2 in which the ratio of said geometrical progression is 0.84.

4. A set of drills as claimed in claim 1 in which at least a part of said stems is provided with at least one guide mark to indicate to the using dentist the depth to which he engages the drill into a dental canal.

* * * * *